United States Patent
Yagi et al.

(10) Patent No.: US 10,611,746 B2
(45) Date of Patent: Apr. 7, 2020

(54) METHOD FOR PRODUCING 2-ACETYL-4H,9H-NAPHTHO[2,3-B]FURAN-4,9-DIONE

(71) Applicant: Sumitomo Dainippon Pharma Co., Ltd., Osaka (JP)

(72) Inventors: Toshikazu Yagi, Mie (JP); Satoshi Suzuki, Tokyo (JP); Hiroto Tatamidani, Osaka (JP); Kazuki Hashimoto, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 16/408,861

(22) Filed: May 10, 2019

(65) Prior Publication Data

US 2019/0263769 A1 Aug. 29, 2019

Related U.S. Application Data

(62) Division of application No. 15/744,366, filed as application No. PCT/JP2016/003346 on Jul. 15, 2016, now Pat. No. 10,329,267.

(30) Foreign Application Priority Data

Jul. 17, 2015 (JP) .................... 2015-142873

(51) Int. Cl.

| | | |
|---|---|---|
| C07D 303/38 | (2006.01) |
| C07D 307/92 | (2006.01) |
| C07C 49/227 | (2006.01) |
| B01J 21/08 | (2006.01) |
| B01J 29/06 | (2006.01) |
| C07B 63/02 | (2006.01) |
| C07B 63/04 | (2006.01) |
| C07C 49/215 | (2006.01) |
| C07C 31/04 | (2006.01) |
| C07C 31/08 | (2006.01) |
| C07C 43/20 | (2006.01) |
| A61K 31/343 | (2006.01) |
| C07C 45/65 | (2006.01) |

(52) U.S. Cl.
CPC ............ *C07D 307/92* (2013.01); *B01J 21/08* (2013.01); *B01J 29/06* (2013.01); *C07B 63/02* (2013.01); *C07B 63/04* (2013.01); *C07C 49/215* (2013.01); *C07C 49/227* (2013.01); *A61K 31/343* (2013.01); *C07B 2200/13* (2013.01); *C07C 31/04* (2013.01); *C07C 31/08* (2013.01); *C07C 43/20* (2013.01); *C07C 45/65* (2013.01)

(58) Field of Classification Search
CPC .. A61K 31/343; C07D 307/92; C07C 49/215; C07C 49/227; C07C 43/20; C07C 31/08; C07C 31/04; B01J 21/08; B01J 29/06; C07B 63/02; C07B 63/04
USPC ........................................................ 549/548
See application file for complete search history.

(56) References Cited

U.S. PATENT DOCUMENTS

| 6,002,053 A | 12/1999 | Rock et al. |
| 2012/0252763 A1 | 10/2012 | Li |
| 2013/0345176 A1 | 12/2013 | Jiang |

FOREIGN PATENT DOCUMENTS

| JP | 4-312567 | 11/1992 |
| JP | 11-180914 | 7/1999 |
| JP | 2008-162985 | 7/2008 |
| JP | 2010-111629 | 5/2010 |
| JP | 2010-539097 | 12/2010 |
| JP | 2013-522325 | 6/2013 |
| JP | 2014-511384 | 5/2014 |
| JP | 2015-506990 | 3/2015 |
| WO | 2009/036099 | 3/2009 |
| WO | 2011/116398 | 9/2011 |
| WO | 2012/119265 | 9/2012 |
| WO | 2013/120229 | 8/2013 |
| WO | 2013/166618 | 11/2013 |
| WO | 2014/169078 | 10/2014 |

OTHER PUBLICATIONS

Hikime, "Recrystallization method and precipitation method", Experimental Chemistry Course (continued) 2, Separation and Purification, Issued Jan. 25, 1967 by Maruzen Co., Ltd., 46 pages, with English translation.
Solvent Handbook, pp. 156-158, 186-189, 292-294, 350-352, 450-451, 568-571, 578-579 and 642-647, Kodansha Co., Ltd., Issued Sep. 1, 1985, with English translation.
International Search Report dated Aug. 16, 2016 in International (PCT) Application No. PCT/JP2016/003346.
Reichardt, Solvents and Solvent Effects in Organic Chemistry, 2003, Third Edition. p. 1-37. (Year: 2003).
Ripin et al., Chem 206, a comprehensive compilation of Bordwell pKa data, 2005, p. 1-6. (Year: 2005).
Office Action dated Aug. 27, 2018 in U.S. Appl. No. 15/744,366.
Notice of Allowance dated Feb. 27, 2019 in U.S. Appl. No. 15/744,366.

*Primary Examiner* — Taylor V Oh

(74) *Attorney, Agent, or Firm* — Wenderoth, Lind & Ponack, L.L.P.

(57) ABSTRACT

The invention addresses the problem of providing a method for producing 2-acetyl-4H,9H-naphtho[2,3-b]furan-4,9-dione that is suited to industrial production. The invention provides a method for producing 2-acetyl-4H,9H-naphtho[2,3-b]furan-4,9-dione by reacting 3-bromo-3-buten-2-one and 2-hydroxy-1,4-naphthoquinone in the presence of a solvent, then obtaining crystals of 2-acetyl-4H,9H-naphtho[2,3-b]furan-4,9-dione by adding an alcohol-based solvent and/or water to the reaction system, and treating the crystals by using a specific adsorbent in the presence of a solvent.

41 Claims, No Drawings

METHOD FOR PRODUCING 2-ACETYL-4H,9H-NAPHTHO[2,3-B]FURAN-4,9-DIONE

TECHNICAL FIELD

The present invention relates to a production method of 2-acetyl-4H,9H-naphtho[2,3-b]furan-4,9-dione useful as a medicament.

BACKGROUND ART

For example, methods described in Patent Literature 1, Patent Literature 2, and Patent Literature 3 are known as the production methods of 2-acetyl-4H,9H-naphtho[2,3-b]furan-4,9-dione.

In Patent Literature 1, Li et al. obtain 3-bromo-3-buten-2-one by brominating 3-buten-2-one with bromine, followed by dehydrobromination using DBU (diazabicycloundecene). They report a method of subsequently performing a coupling reaction of 3-bromo-3-buten-2-one and 2-hydroxy-1,4-naphthoquinone with additional DBU added, and then obtaining a solid by crystallization to crystallize the obtained solid, thereby obtaining 2-acetyl-4H,9H-naphtho[2,3-b]furan-4,9-dione.

In Patent Literature 2, Li et al. obtain 3-bromo-3-buten-2-one by brominating 3-buten-2-one with bromine, and then performing dehydrobromination using DBU. Subsequently, 3-bromo-3-buten-2-one and 2-hydroxy-1,4-naphthoquinone are coupled with DBU, and a crude mixture of 2-acetyl-4H,9H-naphtho[2,3-b]dihydrofuran-4,9-dione and 2-acetyl-4H,9H-naphtho[2,3-b]furan-4,9-dione is obtained by crystallization. This crude mixture is oxidized with manganese dioxide to obtain 2-acetyl-4H,9H-naphtho[2,3-b]furan-4,9-dione, which is then treated with ethyl acetate to obtain 2-acetyl-4H,9H-naphtho [2,3-b]furan-4,9-dione.

In Patent Literature 3, Jiang et al. obtain 2-acetyl-4H,9H-naphtho[2,3-b]dihydrofuran-4,9-dione by brominating 3-buten-2-one with bromine, and performing dehydrobromination with DBU to obtain 3-bromo-3-buten-2-one, and then adding 2-hydroxy-1,4-naphthoquinone into the reaction system, followed by condensation under an air atmosphere. Subsequently, 2-acetyl-4H,9H-naphtho[2,3-b]dihydrofuran-4,9-dione is stirred under an air atmosphere with DBU to obtain 2-acetyl-4H,9H-naphtho[2,3-b]furan-4,9-dione.

All of these production methods have a low yield, and they are not recognized as methods that can efficiently produce target substances in an industrial scale.

CITATION LIST

Patent Literature

[PTL 1]
International Publication No. WO 2009/036099
[PTL 2]
International Publication No. WO 2011/116398
[PTL 3]
International Publication No. WO 2012/119265

SUMMARY OF INVENTION

Solution to Problem

The present invention provides a production method of 2-acetyl-4H,9H-naphtho[2,3-b]furan-4,9-dione suitable for industrial production. More specifically, the present invention provides a method of producing highly pure 2-acetyl-4H,9H-naphtho[2,3-b]furan-4,9-dione in a high yield with a safe and simple operation method, which can be applied to commercialized production.

In detail, as a result of earnest investigation, the present inventors have discovered that a crystal of 2-acetyl-4H,9H-naphtho[2,3-b]furan-4,9-dione can be obtained in a good yield by adding an alcohol-based solvent and/or water when reacting 3-bromo-3-buten-2-one and 2-hydroxy-1,4-naphthoquinone in the presence of a solvent. Furthermore, it was surprisingly discovered that treatment of the obtained crystal with an adsorbent in the presence of a solvent improves yield.

Specifically, the present invention is as described below.
[Item 1]
A production method of 2-acetyl-4H,9H-naphtho[2,3-b]furan-4,9-dione comprising the following step (c):
(c) reacting 3-bromo-3-buten-2-one, 2-hydroxy-1,4-naphthoquinone, and a base in the presence of a non-alcohol, non-ketone-based solvent A, and adding an alcohol-based solvent B and/or water to obtain a crystal of 2-acetyl-4H,9H-naphtho[2,3-b]furan-4,9-dione.
[Item 2]
The production method according to item 1, wherein in the step (c), an oxidant is added to a reaction solution after the addition of the alcohol-based solvent B and/or water.
[Item 3]
The production method according to item 2, wherein the oxidant is at least one selected from the group consisting of oxygen, hydrogen peroxide, sodium hypochlorite, sodium chlorite, chlorine, iodine, nitric acid, and potassium nitrate.
[Item 4] The production method according to item 3, wherein the oxidant is oxygen.
[Item 5]
The production method according to item 1, wherein in the step (c), a gas having an oxygen concentration of 1-25% is added to the reaction solution after the addition of the alcohol-based solvent B and/or water.
[Item 6]
The production method according to item 5, wherein the gas having an oxygen concentration of 1-25% is a gas comprising an inactive gas as a component other than oxygen.
[Item 7]
The production method according to item 6, wherein the inactive gas is nitrogen and/or argon.
[Item 8]
The production method according to item 5, wherein the gas having an oxygen concentration of 1-25% is air.
[Item 9]
The production method according to any one of items 1 to 8, further comprising the following step (d) after the step (c):
(d) purifying 2-acetyl-4H,9H-naphtho[2,3-b]furan-4,9-dione obtained in the step (c), using an adsorbent in the presence of a non-alcohol-based solvent C.
[Item 10]
The production method according to item 9, further comprising the following step (e) after the step (d):
(e) removing the adsorbent used in the step (d) and evaporating the non-alcohol-based solvent C.
[Item 11] The production method according to item 10, further comprising the following step (f) after the step (e):
(f) crystallizing 2-acetyl-4H,9H-naphtho[2,3-b]furan-4,9-dione obtained in the step (e) by adding at least one crystallization solvent D selected from a hydrocarbon-based solvent, an alcohol-based solvent, an acid-based solvent, an ester-based solvent, an ether-based solvent, and water, to obtain 2-acetyl-4H,9H-naphtho[2,3-b]furan-4,9-dione.

[Item 12]

The production method according to item 11, further comprising the following step (g) after the step (f):

(g) slurrying 2-acetyl-4H,9H-naphtho[2,3-b]furan-4,9-dione obtained in the step (f) with ethyl acetate to form a crystal of 2-acetyl-4H,9H-naphtho[2,3-b]furan-4,9-dione.

[Item 13]

The production method according to any one of items 1-12, wherein the non-alcohol, non-ketone-based solvent A used in the step (c) is at least one selected from the group consisting of a halogen-based solvent, an amide-based solvent, a nitrile-based solvent, a sulfoxide-based solvent, an ether-based solvent, an ester-based solvent, and a hydrocarbon-based solvent.

[Item 14]

The production method according to item 13, wherein the non-alcohol, non-ketone-based solvent A used in the step (c) is at least one selected from the group consisting of chloroform, dichloromethane, carbon tetrachloride, monochlorobenzene, N,N-dimethylacetamide, N,N-dimethylformamide, N-methyl-2-pyrrolidone, acetonitrile, propionitrile, dimethyl sulfoxide, diethyl sulfoxide, diisopropyl ether, tert-butyl methyl ether, cyclopentyl ethyl ether, cyclopentyl methyl ether, tetrahydrofuran, 2-methyltetrahydrofuran, 1,4-dioxane, anisole, methyl acetate, ethyl acetate, propyl acetate, butyl acetate, toluene, and xylene.

[Item 15]

The production method according to item 14, wherein the non-alcohol, non-ketone-based solvent A used in the step (c) is at least one selected from the group consisting of chloroform, monochlorobenzene, N,N-dimethylacetamide, N-methyl-2-pyrrolidone, acetonitrile, tert-butyl methyl ether, tetrahydrofuran, 2-methyltetrahydrofuran, anisole, ethyl acetate, toluene, and xylene.

[Item 16]

The production method according to item 15, wherein the non-alcohol, non-ketone-based solvent A used in the step (c) is at least one selected from the group consisting of monochlorobenzene and acetonitrile.

[Item 17]

The production method according to any one of items 1 to 16, wherein in the step (c), 0.8 equivalent to 1.2 equivalents of 2-hydroxy-1,4-naphthoquinone is reacted in a molar ratio to 3-bromo-3-buten-2-one.

[Item 18]

The production method according to item 17, wherein in the step (c), 0.9 equivalent to 1.1 equivalents of 2-hydroxy-1,4-naphthoquinone is reacted in a molar ratio to 3-bromo-3-buten-2-one.

[Item 19]

The production method according to any one of items 1 to 18, wherein the base used in the step (c) is diazabicycloundecene.

[Item 20]

The production method according to item 19, wherein diazabicycloundecene used in the step (c) has a molar ratio of 0.9 equivalent to 5.0 equivalents to 3-bromo-3-buten-2-one.

[Item 21]

The production method according to item 20, wherein in the step (c), 0.9 equivalent to 1.5 equivalents of diazabicycloundecene in a molar ratio to 3-bromo-3-buten-2-one is added to the reaction solution of 3-bromo-3-buten-2-one and 2-hydroxy-1,4-naphthoquinone, and after stirring for one minute to three hours, 0.01 equivalent to 1.0 equivalent of diazabicycloundecene is further added in a molar ratio to 3-bromo-3-buten-2-one.

[Item 22]

The production method according to any one of items 1 to 21, wherein the alcohol-based solvent B used in the step (c) is methanol, ethanol, 1-propanol, 2-propanol, n-butyl alcohol, or isobutyl alcohol, or mixtures thereof.

[Item 23]

The production method according to item 22, wherein the alcohol-based solvent B used in the step (c) is methanol or ethanol, or mixtures thereof.

[Item 24]

The production method according to any one of items 9 to 23, wherein the non-alcohol-based solvent C used in the step (d) is at least one selected from the group consisting of an ether-based solvent, an amide-based solvent, a ketone-based solvent, a halogen-based solvent, a sulfoxide-based solvent, an ester-based solvent, a hydrocarbon-based solvent, and a nitrile-based solvent.

[Item 25]

The production method according to item 24, wherein the non-alcohol-based solvent C used in the step (d) is at least one selected from the group consisting of chloroform, dichloromethane, carbon tetrachloride, monochlorobenzene, N,N-dimethylacetamide, N,N-dimethylformamide, N-methyl-2-pyrrolidone, acetonitrile, propionitrile, dimethyl sulfoxide, diethyl sulfoxide, diisopropyl ether, tert-butyl methyl ether, cyclopentyl ethyl ether, cyclopentyl methyl ether, tetrahydrofuran, 2-methyltetrahydrofuran, 1,4-dioxane, anisole, methyl acetate, ethyl acetate, propyl acetate, butyl acetate, toluene, xylene, acetone, methyl ethyl ketone, and methyl isobutyl ketone.

[Item 26]

The production method according to item 24, wherein the non-alcohol-based solvent C used in the step (d) is at least one selected from the group consisting of N,N-dimethylacetamide, N,N-dimethylformamide, anisole, ethyl acetate, propyl acetate, and butyl acetate.

[Item 27]

The production method according to item 24, wherein the non-alcohol-based solvent C used in the step (d) is anisole.

[Item 28]

The production method according to any one of items 9 to 27, wherein the adsorbent used in the step (d) is at least one selected from the group consisting of activated alumina, zeolite, activated carbon, and silica gel.

[Item 29]

The production method according to item 28, wherein the adsorbent used in the step (d) is silica gel.

[Item 30]

The production method according to any one of items 9 to 29, wherein the adsorbent used in the step (d) is a 0.01 to 0.3-fold amount in a weight ratio to 2-acetyl-4H,9H-naphtho[2,3-b]furan-4,9-dione.

[Item 31]

The production method according to item 30, wherein the adsorbent used in the step (d) is a 0.02 to 0.2-fold amount in a weight ratio to 2-acetyl-4H,9H-naphtho[2,3-b]furan-4,9-dione.

[Item 32]

The production method according to any one of items 11 to 31, wherein the crystallization solvent D used in the step (f) is at least one selected from the group consisting of n-heptane, xylene, n-butanol, isobutyl acetate, toluene, cyclohexane, acetic acid, methanol, ethanol, 1-propanol, 2-propanol, n-butyl alcohol, isobutyl alcohol, and water.

[Item 33]

The production method according to item 32, wherein the crystallization solvent D used in the step (f) comprises n-heptane.

[Item 34]

The production method according to item 32, wherein the crystallization solvent D used in the step (f) comprises xylene.

[Item 35]

The production method according to item 32, wherein the crystallization solvent D used in the step (f) comprises n-butanol.

[Item 36]

The production method according to item 32, wherein the crystallization solvent D used in the step (f) comprises isobutyl acetate.

[Item 37]

The production method according to any one of items 1 to 36, further comprising the following steps (a) and (b) before the step (c):

(a) reacting 3-buten-2-one and bromine to form 3,4-dibromobutan-2-one; and (b) reacting 3,4-dibromobutan-2-one obtained in the step (a) with a base to undergo dehydrobromination thereby forming 3-bromo-3-buten-2-one.

[Item 38]

The production method according to item 37, wherein the base used in the step (b) is at least one selected from the group consisting of triethylamine, diisopropylethylamine, N-methylpyrrolidine, diazabicyclo[2.2.2]octane, N-methylmorpholine, and inorganic bases.

[Item 39]

The production method according to item 38, wherein the base used in the step (b) is N-methylmorpholine.

In the present invention, it is intended that in addition to the clarified combinations, the above-mentioned one or more characteristics can be further combined and provided. These further embodiments and advantages of the present invention will be recognized by those skilled in the art if the following detailed descriptions are read and understood as necessary.

Advantageous Effects of Invention

According to the production method of the present invention, 2-acetyl-4H, 9H-naphtho[2,3-b]furan-4,9-dione which is useful as a medicament can be produced inexpensively and safely. Furthermore, according to the production method of the present invention, 2-acetyl-4H, 9H-naphtho[2,3-b]furan-4,9-dione can be produced in a high yield and with high purity compared to known production methods.

DESCRIPTION OF EMBODIMENTS

Hereinafter, the present invention will be explained while showing its preferred embodiments. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

The terms in the present specification are described below.

An "adsorbent" refers to a substance having a strong property of adsorbing other substance on its surface.

Specific examples of the "adsorbent" include, but are not limited to, activated alumina, zeolite, activated carbon, silica gel, mixtures thereof, and the like. The specific examples include, preferably, zeolite, activated carbon, and silica gel; more preferably, activated carbon and silica gel; and most preferably, silica gel.

A "base" includes both organic bases and inorganic bases.

Specific examples of the "base" include, but are not limited to, triethylamine, diisopropylethylamine, N-methylpyrrolidine, 1,4-diazabicyclo[2.2.2]octane, N-methylmorpholine, diazabicycloundecene, inorganic bases, mixtures thereof, and the like. The specific examples include, preferably, triethylamine, diisopropylethylamine, N-methylpyrrolidine, 1,4-diazabicyclo[2.2.2]octane, diazabicycloundecene, and N-methylmorpholine; more preferably, triethylamine, diisopropylethylamine, diazabicycloundecene, and N-methylmorpholine; and most preferably, diazabicycloundecene and N-methylmorpholine.

Specific examples of the "inorganic bases" include lithium hydroxide, sodium hydroxide, calcium hydroxide, barium hydroxide, sodium carbonate, sodium hydrogen carbonate, and cesium carbonate. The specific examples preferably include, but are not limited to, lithium hydroxide, sodium hydroxide, sodium carbonate, sodium hydrogen carbonate, cesium carbonate, mixtures thereof, and the like. The specific examples include, more preferably, sodium hydroxide, sodium carbonate, and sodium hydrogen carbonate; and most preferably, sodium hydroxide and sodium carbonate.

Specific examples of a "hydrocarbon-based solvent" include, but are not limited to, n-heptane, n-hexane, toluene, xylene, cyclopentane, cyclohexane, mixtures thereof, and the like. The specific examples include, preferably, n-heptane, toluene, xylene, and cyclohexane; more preferably, n-heptane, toluene, and xylene; and most preferably, n-heptane and xylene.

Specific examples of an "alcohol-based solvent" include, but are not limited to, methanol, ethanol, 1-propanol, 2-propanol, n-butyl alcohol, isobutyl alcohol, mixtures thereof, and the like. The specific examples include, preferably, methanol, ethanol and n-butyl alcohol; more preferably, ethanol and n-butyl alcohol; and most preferably, ethanol.

Specific examples of a "ketone-based solvent" include, but are not limited to, acetone, methyl ethyl ketone, diethyl ketone, methyl propyl ketone, methyl amyl ketone, cyclohexanone, methyl isobutyl ketone, mixtures thereof, and the like. The specific examples include, preferably, acetone, methyl ethyl ketone, diethyl ketone, methyl propyl ketone, and methyl isobutyl ketone; more preferably, methyl ethyl ketone and methyl isobutyl ketone; and most preferably, methyl ethyl ketone.

Specific examples of an "ether-based solvent" include, but are not limited to, diisopropyl ether, tert-butyl methyl ether, cyclopentyl ethyl ether, cyclopentyl methyl ether, tetrahydrofuran, 2-methyltetrahydrofuran, 1,4-dioxane, anisole, mixtures thereof, and the like. The specific examples include, preferably, 2-methyltetrahydrofuran, tetrahydrofuran, and anisole; more preferably, tetrahydrofuran and anisole; and most preferably, anisole.

Specific examples of an "ester-based solvent" include, but are not limited to, methyl acetate, ethyl acetate, propyl acetate, butyl acetate, isobutyl acetate, mixtures thereof, and the like. The specific examples include, preferably, ethyl acetate, propyl acetate, and isobutyl acetate; more preferably, ethyl acetate and isobutyl acetate; and most preferably, isobutyl acetate.

Specific examples of a "halogen-based solvent" include, but are not limited to, chloroform, dichloromethane, carbon tetrachloride, monochlorobenzene, mixtures thereof, and the like. The specific examples include, preferably, chloroform, carbon tetrachloride, and monochlorobenzene; more preferably, chloroform and monochlorobenzene; and most preferably, monochlorobenzene.

Specific examples of an "amide-based solvent" include, but are not limited to, N,N-dimethylacetamide, N,N-dimethylformamide, N-methyl-2-pyrrolidone, mixtures thereof, and the like. The specific examples include, preferably, N,N-dimethylformamide and N-methyl-2-pyrrolidone; and most preferably, N-methyl-2-pyrrolidone.

Specific examples of a "nitrile-based solvent" include, but are not limited to, acetonitrile, propionitrile, mixtures thereof, and the like. The specific examples include, most preferably, acetonitrile.

Specific examples of a "sulfoxide-based solvent" include, but are not limited to, dimethyl sulfoxide, diethyl sulfoxide, mixtures thereof, and the like. The specific examples include, most preferably, dimethyl sulfoxide.

A "non-alcohol, non-ketone-based solvent" refers to a solvent that is neither an alcohol-based solvent nor a ketone-based solvent. The non-alcohol, non-ketone-based solvent representatively includes, but is not limited to, a halogen-based solvent, an amide-based solvent, a nitrile-based solvent, a sulfoxide-based solvent, an ether-based solvent, an ester-based solvent, a hydrocarbon-based solvent, mixtures thereof, and the like. Specific examples of the "non-alcohol, non-ketone-based solvent" include, but are not limited to, chloroform, dichloromethane, carbon tetrachloride, monochlorobenzene, N,N-dimethylacetamide, N,N-dimethylformamide, N-methyl-2-pyrrolidone, acetonitrile, propionitrile, dimethyl sulfoxide, diethyl sulfoxide, diisopropyl ether, tert-butyl methyl ether, cyclopentyl ethyl ether, cyclopentyl methyl ether, tetrahydrofuran, 2-methyltetrahydrofuran, 1,4-dioxane, anisole, methyl acetate, ethyl acetate, propyl acetate, butyl acetate, toluene, xylene, mixtures thereof, and the like.

A "non-alcohol-based solvent" refers to a solvent that is not an alcohol-based solvent. The non-alcohol-based solvent representatively includes, but is not limited to, a halogen-based solvent, an amide-based solvent, a nitrile-based solvent, a sulfoxide-based solvent, an ether-based solvent, an ester-based solvent, a hydrocarbon-based solvent, a ketone-based solvent, mixtures thereof, and the like. Specific examples of the "non-alcohol-based solvent" include, but are not limited to, chloroform, dichloromethane, carbon tetrachloride, monochlorobenzene, N,N-dimethylacetamide, N,N-dimethylformamide, N-methyl-2-pyrrolidone, acetonitrile, propionitrile, dimethyl sulfoxide, diethyl sulfoxide, diisopropyl ether, tert-butyl methyl ether, cyclopentyl ethyl ether, cyclopentyl methyl ether, tetrahydrofuran, 2-methyltetrahydrofuran, 1,4-dioxane, anisole, methyl acetate, ethyl acetate, propyl acetate, butyl acetate, toluene, xylene, acetone, methyl ethyl ketone, methyl isobutyl ketone, mixtures thereof, and the like.

A "crystallization solvent" refers to a solvent that is used at the time of crystallization. The crystallization solvent representatively includes, but is not limited to, a hydrocarbon-based solvent, an alcohol-based solvent, an ether-based solvent, an ester-based solvent, an acid-based solvent, water, mixtures thereof, and the like. The examples thereof preferably include, but are not limited to, n-heptane, xylene, toluene, cyclohexane, n-butanol, methanol, ethanol, 1-propanol, 2-propanol, n-butyl alcohol, isobutyl alcohol, isobutyl acetate, acetic acid, water, mixtures thereof, and the like. The examples thereof include, more preferably, n-heptane, xylene, n-butanol, and isobutyl acetate; further preferably, n-heptane and xylene; and most preferably, n-heptane.

The "acid-based solvent" refers to a solvent that is an acid. Examples of the acid-based solvent include, but are not limited to, formic acid, acetic acid, mixtures thereof, and the like. The examples include, most preferably, acetic acid.

An "aprotic solvent" refers to a solvent having an extremely weak property of releasing protons or providing hydrogen bonds. Examples of the aprotic solvent include, but are not limited to, N,N-dimethylacetamide, N,N-dimethylformamide, N-methyl-2-pyrrolidone, acetonitrile, propionitrile, dimethyl sulfoxide, diethyl sulfoxide, mixtures thereof, and the like. The examples include, most preferably, acetonitrile.

With regard to an expression for solvents and the like as used herein, it is understood that the expression, "is at least one selected from . . . ", encompasses mixtures of two or more options when those two or more options are selected from the options thereof.

An "oxidant" refers to a reagent that takes away an electron of a substance. Examples thereof include, oxygen, hydrogen peroxide, sodium hypochlorite, sodium chlorite, chlorine, iodine, nitric acid, and potassium nitrate. The examples are, preferably, oxygen, hydrogen peroxide, sodium hypochlorite, and nitric acid; and most preferably, oxygen.

An "inactive gas" refers to a gas having low chemical reactivity. Examples thereof include, nitrogen, helium, neon, argon, krypton, and xenon. The examples are, preferably, nitrogen and argon; and most preferably, nitrogen.

A "gas having an oxygen concentration of 1-25%" refers to a gas resulting from dilution of pure oxygen to a volume fraction of 1-25% by the inactive gas. Examples thereof include, 1-25% oxygen/nitrogen and 1-25% oxygen/argon. The examples are, preferably, 1-15% oxygen/nitrogen and 1-15% oxygen/argon; and further preferably, 1-10% oxygen/nitrogen and 1-10% oxygen/argon.

Next, the present invention will be explained in more detail with its preferred embodiments. However, the technical scope of the present invention is not limited to those preferred embodiments. In addition, alterations can be made in a range that does not deviate from the scope of the present invention. It is noted that compound names shown in the following preferred examples do not always follow the IUPAC nomenclature.

In the present specification, the following abbreviations may be used to simplify a description. DBU: diazabicycloundecene, DMF: N,N-dimethylformamide.

Representative Production Method of the Present Invention

Production Method of 2-acetyl-4H,9H-naphtho[2,3-b]furan-4,9-dione

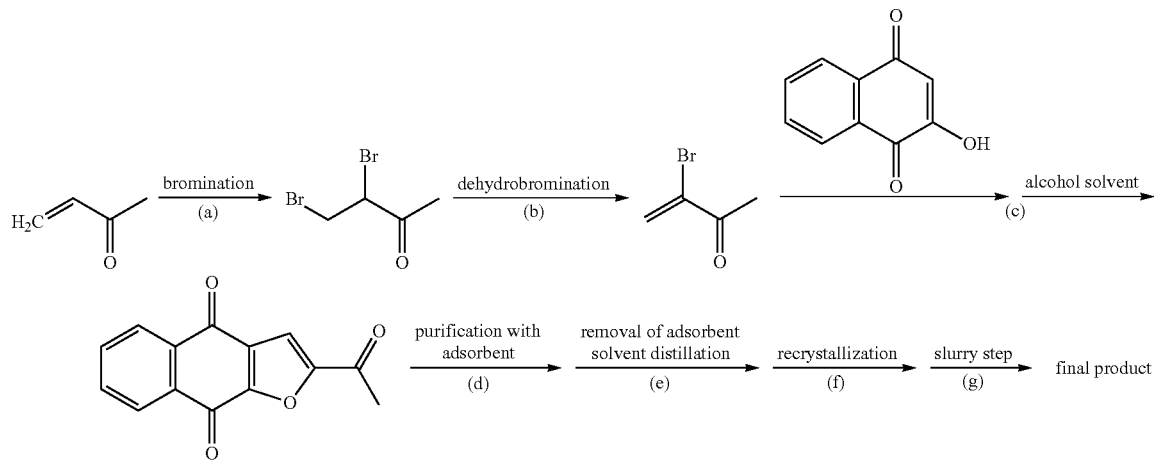

[Chem. 1]

As will be discussed below, it is understood that steps (c) and (d) are most important in the method of the present invention, and other steps may be replaced with different steps. Additionally, steps (a)-(g) will be explained below with their preferred embodiments, but the present invention is not limited thereto.

Step (a)

The present step is an optional step in the present invention of reacting a compound, 3-buten-2-one, with bromine in the presence of an appropriate solvent to obtain a reaction solution of 3,4-dibromobutan-2-one. Examples of a solvent used in the present step include a halogen-based solvent and the like such as chloroform, dichloromethane, carbon tetrachloride, monochlorobenzene, and the like. The examples include, preferably, chloroform, dichloromethane, and monochlorobenzene; and more preferably, monochlorobenzene. The amount of bromine used is generally 0.8 equivalent to 5 equivalents, preferably 0.8 equivalent to 3 equivalents, and more preferably 0.9 equivalent to 2 equivalents, in a molar ratio to one equivalent of 3-buten-2-one. The reaction time is generally about 0.1 hour to 12 hours, preferably 0.1 hour to 4 hours, and more preferably 0.1 hour to 1 hour. The reaction temperature is generally −70° C. to 100° C., preferably about −40° C. to about 80° C., and more preferably about −20° C. to about 30° C.

Step (b)

The present step is an optional step in the present invention of adding a base to the reaction solution of 3,4-dibromobutan-2-one, which can be obtained in the above-described production step (a) (may be acquired through another route), to undergo dehydrobromination thereby forming 3-bromo-3-buten-2-one. Examples of the base used in the present step include triethylamine, diisopropylethylamine, N-methylpyrrolidine, 1,4-diazabicyclo[2.2.2]octane, N-methylmorpholine, and inorganic bases. The examples include, preferably, triethylamine, diisopropylethylamine, N-methylpyrrolidine, 1,4-diazabicyclo[2.2.2]octane, and N-methylmorpholine; and more preferably, N-methylmorpholine. The amount of the base used is generally 0.8 equivalent to 5 equivalents, preferably 0.8 equivalent to 3 equivalents, and more preferably 0.9 equivalent to 2 equivalents, in a molar ratio to one equivalent of 3,4-dibromobutan-2-one. The reaction time is generally about 0.1 hour to about 24 hours, preferably 0.1 hour to 8 hours, and more preferably 0.1 hour to 2 hours. The reaction temperature is generally −40° C. to about 80° C., preferably −20° C. to 50° C., and more preferably 0° C. to 50° C.

Step (c)

The present step is a step of reacting 2-hydroxy-1,4-naphthoquinone with 3-bromo-3-buten-2-one, which can be obtained in the above-described production step (b) (may be produced through another route), in the presence of an appropriate non-alcohol, non-ketone-based solvent A and a base to form 2-acetyl-4H,9H-naphtho[2,3-b]furan-4,9-dione, and then adding thereto an alcohol-based solvent B and/or water to obtain a crystal of 2-acetyl-4H,9H-naphtho[2,3-b]furan-4,9-dione. The present step is one important step of the present invention, and the use of the alcohol-based solvent B and/or water enables production of 2-acetyl-4H,9H-naphtho[2,3-b]furan-4,9-dione with a high yield and increased purity. Examples of the non-alcohol, non-ketone-based solvent A used in the present step include a halogen-based solvent such as chloroform, dichloromethane, carbon tetrachloride, monochlorobenzene, and the like; an aprotic solvent such as N,N-dimethylacetamide, N,N-dimethylformamide, N-methyl-2-pyrrolidone, acetonitrile, propionitrile, dimethyl sulfoxide, diethyl sulfoxide, and the like; an ether-based solvent such as diisopropyl ether, tert-butyl methyl ether, cyclopentyl ethyl ether, cyclopentyl methyl ether, tetrahydrofuran, 2-methyltetrahydrofuran, 1,4-dioxane, anisole, and the like; an ester-based solvent such as methyl acetate, ethyl acetate, propyl acetate, butyl acetate, and the like; a hydrocarbon-based solvent such as toluene, xylene, and the like; mixed solvents thereof; and the like. The examples include, preferably, chloroform, N,N-dimethylacetamide, N-methyl-2-pyrrolidone, acetonitrile, tert-butyl methyl ether, tetrahydrofuran, 2-methyltetrahydrofuran, anisole, ethyl acetate, toluene, and xylene; and more preferably, monochlorobenzene and acetonitrile. Examples of the base used in the present step include DBU. Examples of the alcohol-based solvent B used in the present step include methanol, ethanol, 1-propanol, 2-propanol, n-butyl alcohol, and isobutyl alcohol; preferably, methanol and ethanol; and more preferably, ethanol. The amount of 2-hydroxy-1,4-naphthoquinone used is generally 0.8 equivalent to 1.2 equivalents, preferably 0.9 equivalent to 1.2 equivalents, and more preferably 0.9 equivalent to 1.1 equivalents, in a molar ratio to 3-bromo-3-buten-2-one. The amount of the base used is generally 0.9 equivalent to 5.0 equivalents, preferably 0.9 equivalent to 3.0 equivalents, more preferably 0.9 equivalent to 2.0 equivalents, further preferably 1.0 equivalent to 1.6 equivalents and 1.0 equivalent to 1.4 equivalents, and most preferably 1.0 equivalent to 1.3 equivalents, in a molar ratio to one equivalent of 3-bromo-3-buten-2-one. The base may be used in a divided manner or in one portion. When the base is used in a divided manner, the amount of the base used is generally 0.9 equivalent to 1.5 equivalents and 0.01 equivalent to 1.0 equivalent, preferably 0.9 equivalent to 1.1 equivalents and 0.01 equivalent to 0.5 equivalent, and more preferably 0.95 equivalent to 1.05 equivalents and 0.01 equivalent to 0.3 equivalent, in a molar ratio to 3-bromo-3-buten-2-one. The reaction time is generally about 0.1 hour to 48 hours, preferably 0.1 hour to 12 hours, and more preferably 0.1 hour to 4 hours. When the base is used in a divided manner, the time from the addition of an initial base until the addition of the remaining base is generally 1 minute to 24 hours, preferably 1 minute to 6 hours, more preferably 1 minute to 3 hours, and most preferably 5 minute to 1 hour. The reaction temperature is generally −20° C. to 120° C., preferably 0° C. to 100° C., and more preferably 30° C. to 80° C. When the base is used in a divided manner, the order of adding an initially added base, the remaining base, and the alcohol-based solvent B and/or water can be in any order. For example, after initially adding a base, the remaining base may be added with an interval of the above-described time, and then the alcohol-based solvent B and/or water may be added; alternatively, after initially adding a base, the alcohol-based solvent B and/or water may be added, and then the remaining base may be added.

Addition of an oxidant to the reaction solution after addition of the alcohol-based solvent B and/or water in the step (c) increases the precipitation amount of 2-acetyl-4H,9H-naphtho[2,3-b]furan-4,9-dione in the solution and improves the yield.

Specific examples of the oxidant include oxygen, hydrogen peroxide, sodium hypochlorite, sodium chlorite, chlorine, iodine, nitric acid, and potassium nitrate. The examples are preferably, oxygen, hydrogen peroxide, sodium hypochlorite, and nitric acid; and most preferably, oxygen.

When the oxidant is oxygen, in the step (c), after the addition of the alcohol-based solvent B and/or water, a gas having an oxygen concentration of 1-25% may be added to the reaction solution.

The gas having an oxygen concentration of 1-25% may be a gas comprising an inactive gas as a component other than oxygen. Specifically, a gas comprising nitrogen, argon, helium, or the like as the component other than oxygen is used.

Air may be used as the gas having an oxygen concentration of 1-25%.

Step (d)

The present step is an optional step of the present invention of dissolving the crystal of 2-acetyl-4H,9H-naphtho[2,3-b]furan-4,9-dione, which has been obtained in the above-described production step (c), in an appropriate non-alcohol-based solvent C, followed by purification with an adsorbent. It should be noted that, in the present invention, the use of the adsorbent in addition to the step (c) enables production of 2-acetyl-4H,9H-naphtho[2,3-b]furan-4,9-dione in a higher yield and with higher purity compared to known production methods.

Examples of the non-alcohol-based solvent C used in the present step include a halogen-based solvent such as chloroform, dichloromethane, carbon tetrachloride, monochlorobenzene, and the like; an aprotic solvent such as N,N-dimethylacetamide, N,N-dimethylformamide, N-methyl-2-pyrrolidone, acetonitrile, propionitrile, dimethyl sulfoxide, diethyl sulfoxide, and the like; an ether-based solvent such as diisopropyl ether, tert-butyl methyl ether, cyclopentyl ethyl ether, cyclopentyl methyl ether, tetrahydrofuran, 2-methyltetrahydrofuran, 1,4-dioxane, anisole, and the like; an ester solvent such as methyl acetate, ethyl acetate, propyl acetate, butyl acetate, and the like; a hydrocarbon-based solvent such as toluene, xylene, and the like; a ketone-based solvent such as acetone, methyl ethyl ketone, methyl isobutyl ketone, and the like; mixed solvents thereof; and the like. The examples include, preferably, N,N-dimethylacetamide, N,N-dimethylformamide, anisole, ethyl acetate, propyl acetate, and butyl acetate; and more preferably, anisole.

Examples of the adsorbent used in the present step include activated alumina, zeolite, activated carbon, and silica gel; preferably, activated alumina, activated carbon, and silica gel; and more preferably, silica gel.

The amount of the adsorbent used is a 0.001 to 0.3-fold amount, preferably a 0.01 to 0.2-fold amount, and more preferably a 0.02 to 0.2-fold amount, in a weight ratio to 2-acetyl-4H,9H-naphtho[2,3-b]furan-4,9-dione.

The purification time is generally about 0.1 hour to 12 hours, preferably 0.1 hour to 8 hours, and more preferably 0.1 hour to 2 hours.

The purification temperature is generally 0° C. to 150° C., preferably 30° C. to 100° C., and more preferably 50° C. to 90° C.

Step (e)

The present step is an optional step of the present invention of removing the adsorbent from the suspension of both 2-acetyl-4H,9H-naphtho[2,3-b]furan-4,9-dione, which has been purified in the above-described production step (d), and the adsorbent, and evaporating the non-alcohol-based solvent C.

Step (f)

The present step is an optional step of the present invention of crystallizing 2-acetyl-4H,9H-naphtho[2,3-b]furan-4,9-dione, which can be obtained in the above-described production step (e), by using an appropriate crystallization solvent D to obtain 2-acetyl-4H,9H-naphtho[2,3-b]furan-4,9-dione.

Examples of the crystallization solvent D used in the present step include n-heptane, xylene, n-butanol, isobutyl acetate, toluene, cyclohexane, acetic acid, methanol, ethanol, 1-propanol, 2-propanol, n-butyl alcohol, isobutyl alcohol, water, mixed solvents thereof, and the like. The examples include, preferably, n-heptane, xylene, n-butanol, and isobutyl acetate; more preferably, n-heptane and xylene; and most preferably, n-heptane.

The crystallization (crystallizing) time is generally about 0.5 hour to 96 hours, preferably 1 hour to 48 hours, and more preferably 1 hour to 24 hours.

The temperature at the time of crystallization (crystallizing) varies depending on the type and the like of the crystallization solvent D to be used. However, the temperature is generally −10° C. to 50° C., preferably 0° C. to 40° C., and more preferably 0° C. to 30° C.

Step (g)

The present step is an optional step of the present invention of slurrying 2-acetyl-4H, 9H-naphtho[2,3-b]furan-4,9-dione, which can be obtained in the above-described production step (f), with ethyl acetate to obtain a crystal of 2-acetyl-4H, 9H-naphtho[2,3-b]furan-4,9-dione.

The time for slurrying is generally about 0.5 hour to 48 hours, preferably 1 hour to 12 hours, and more preferably 1 hour to 8 hours.

The temperature of slurrying is generally 0° C. to 150° C., preferably 20° C. to 120° C., and more preferably 40° C. to 100° C.

While not wishing to be bound by theory, the present invention discovers that the predetermined effect of the present invention can be achieved by performing the above-described steps (c) and (d). Accordingly, it is understood that steps other than the steps (c) and (d) may not be carried out as stated above.

Accordingly, the present invention provides a production method of 2-acetyl-4H, 9H-naphtho[2,3-b]furan-4,9-dione comprising the step (c): reacting 3-bromo-3-buten-2-one, 2-hydroxy-1,4-naphthoquinone, and a base in the presence of a non-alcohol, non-ketone-based solvent A, following by the addition of an alcohol-based solvent B and/or water to obtain a crystal of 2-acetyl-4H, 9H-naphtho[2,3-b]furan-4, 9-dione. In particular, in the present invention, a crystal of 2-acetyl-4H, 9H-naphtho[2,3-b]furan-4,9-dione can be obtained in a good yield by adding an alcohol-based solvent and/or water when reacting 3-bromo-3-buten-2-one and 2-hydroxy-1,4-naphthoquinone in the presence of a solvent. Improvement of a yield can be recognized as compared to the case without the use of an alcohol-based solvent and/or water. Furthermore, the present invention discovered that the treatment of the obtained crystal with an adsorbent in the presence of a solvent surprisingly improves a yield. Accordingly, in the present invention, yield is improved by including the step (c) and the step (d). While not wishing to be bound by theory, the present invention has discovered that the predetermined effect of the present invention can be achieved by performing the above-described step (c) and the step (d), and this is also demonstrated in the Examples.

In a preferred embodiment, the step (e) may be performed subsequent to the step (d) of the present invention. In the step (e), the adsorbent used in the step (d) is removed, and the non-alcohol-based solvent C is evaporated. Any removal method in the art may be used for the removal of the adsorbent. For example, since the adsorbent is representatively a solid, it can be removed by separating the solid by any method from other components, e.g., a solvent comprising a product. Alternatively, as also exemplified in the Examples and the like, a technique such as hot filtration may be used. Any technique (e.g., vacuum concentration) for solvent evaporation used in the art may also be used for the evaporation of the non-alcohol-based solvent C.

In a further preferred embodiment, the above-described step (f) may be performed after the step (e). In this step (f), 2-acetyl-4H, 9H-naphtho[2,3-b]furan-4,9-dione, which can be obtained in the step (e), is crystallized by adding the crystallization solvent D to obtain 2-acetyl-4H, 9H-naphtho[2,3-b]furan-4,9-dione.

3-bromo-3-buten-2-one and 2-hydroxy-1,4-naphthoquinone used in the step (c) of the present invention may be acquired in any manner. Preferably, 3-bromo-3-buten-2-one produced by the step (b) is used.

Accordingly, in the further preferred embodiment, with regard to 3-bromo-3-buten-2-one used in the step (c), one produced by the above-described step (b) using 3,4-dibromobutan-2-one produced by the step (a) is used.

Furthermore, since all of the steps from (a) to (g) utilized in the present invention contribute to inexpensive and safe production, as long as any combination (may be all) among the steps (a) to (g) is used, 2-acetyl-4H, 9H-naphtho[2,3-b]furan-4,9-dione useful as a medicament can be inexpensively and safely produced as compared to conventional methods. Moreover, 2-acetyl-4H, 9H-naphtho[2,3-b]furan-4,9-dione can be produced in a high yield and with high purity by performing the step (c); preferably the step (d) in addition to this step; further preferably the step (e) in addition to these steps; still further preferably the step (f) in addition to these steps; more preferably the step (g) in addition to these steps; even more preferably the step (b) in addition to these steps; and most preferably the step (a) to the step (g).

The order of adding a reagent and the like is not limited to that previously mentioned.

Hereinafter, the present invention will be further specifically described with Reference examples and Examples. However, these do not limit the present invention. The identification of a compound was performed with an elemental analysis value, a mass spectrum, a high performance liquid chromatography mass spectrometer; LCMS, IR spectra, NMR spectra, high performance liquid chromatography (HPLC), and the like.

In order to simplify the description of the specification, abbreviations as shown below may be used in the Reference examples, the Examples, and the table of the Examples. With regard to signs used for NMR, s refers to a singlet and m refers to a multiplet.

The measurement conditions of the high performance liquid chromatography; HPLC are as shown below, and the retention time of 2-acetyl-4H,9H-naphtho[2,3-b]furan-4,9-dione is shown in Rt (min). Further, the measurement conditions used for the measurement are additionally noted for each actual measurement value. Furthermore, in the following descriptions, HPLC purity (area %) refers to purity that is calculated by comparing each peak area with the measurement conditions described below.

Column: phenomenex Luna 5 u C18(2) 100 A (4.6 mm×250 mm, 5 μm) (manufactured by Waters)
Solvent: solution A: 10 mmol/L $K_2HPO_4$ aqueous solution (pH 6.8), solution B: acetonitrile
Gradient Condition:

TABLE 1

| Minutes | A (%) | B (%) |
|---|---|---|
| 0-5 | 80 | 20 |
| 5-19 | 80→26 | 20→74 |
| 19-35 | 26 | 74 |
| 35-40 | 26→80 | 74→20 |
| 40-55 | 80 | 20 |

Flow rate: 0.8 mL/min
Rt: 23 minutes
Column temperature: 30° C.
Wavelength: 270 nm The Rt of 2-acetyl-4H,9H-naphtho[2,3-b]furan-4,9-dione, which was measured under the above-described conditions, was 23 minutes.

EXAMPLES

Next, the present invention will be described in further detail with its Examples and Comparative examples. However, the technical scope of the present invention is not limited to these examples. In addition, alterations can be made within the scope that does not depart from the scope of the present invention. Further, compound names shown in the following Examples and Comparative examples do not always follow the IUPAC nomenclature.

Example 1-1: Various Production Methods of a Crude Crystal of 2-acetyl-4H,9H-naphtho[2,3-b]furan-4,9-dione

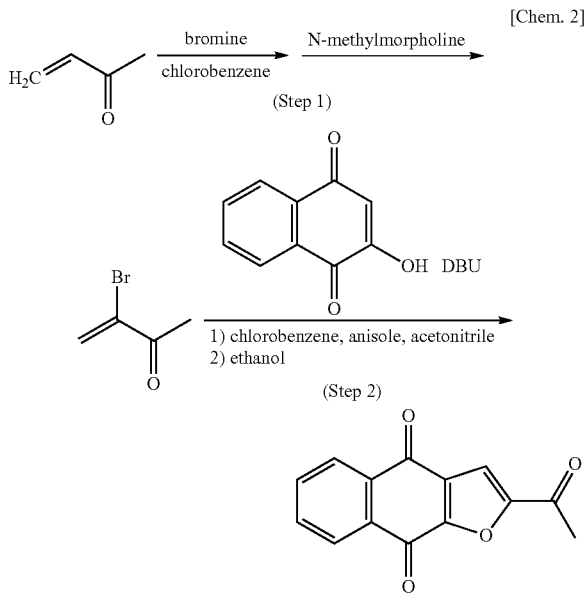

[Chem. 2]

(Step 1)

To monochlorobenzene (2565 g) cooled to −15° C. to −10° C., methyl vinyl ketone (445.7 g, 6.041 mol) having a purity of 95% was added, and bromine (946.1 g, 5.920 mol) was added dropwise over about 3.5 hours at −15° C. to −4° C. Subsequently, a mixed solution of N-methylmorpholine (672.1 g, 6.645 mol) and water (91.9 g) was added dropwise over 2 hours to the reaction solution, followed by stirring for 1 hour at −5° C. After adding water (331.5 g) to the resulting slurry, extraction of the organic layer by a liquid separating operation gave a solution of 3-bromo-3-buten-2-one in monochlorobenzene (3595.2 g, content: 23.1%, yield: 92.2%).

(Step 2)

To 2-hydroxy-1,4-naphthoquinone (100.0 g, 574.2 mmol), acetonitrile (150 g) and DBU (92.0 g) were added, and then the solution of 3-bromo-3-buten-2-one in monochlorobenzene (364.7 g, fineness: 83.88 g, 563.0 mmol) cooled to −15° C. to −10° C. was added dropwise over 20 minutes at 45° C. Subsequently, DBU (10.0 g) was added dropwise at 42° C. to the reaction solution, followed by vacuum concentration at 25° C. to 45° C. to evaporate the solvent (228 g). Ethanol (250 g) was added dropwise at 35° C. to the reaction solution, and after cooling to 10° C., the slurry was filtered to give a wet crystal. The wet crystal was washed with ethanol (85 g), 50% ethanol-water (100 g), and ethanol (85 g), sequentially, and then dried under reduced pressure to give a crude crystal of 2-acetyl-4H, 9H-naphtho[2,3-b]furan-4,9-dione (57.83 g, 240.9 mmol, HPLC purity: 99.70 area %) (yield: 42.8%). Overall yield based on methyl vinyl ketone: 39.5%.

$^1$H-NMR (400 MHz, DMSO-$d_6$) δ: 2.60 (3H, s), 7.90-7.94 (2H, m), 8.04 (1H, s), 8.12-8.17 (2H, m).

Example 1-2: Various Production Methods of a Crude Crystal of 2-acetyl-4H,9H-naphtho[2,3-b]furan-4,9-dione (Step 1)

To isopropyl acetate (4000 g) cooled to −15° C. to −10° C., methyl vinyl ketone (1043 g, 13.4 mol) having a purity of 90.2% was added, and bromine (2102 g, 13.2 mol) was added dropwise over about 2 hours at −15° C. to −4° C. At that time, the reagent was washed and poured with 300 g of isopropyl acetate. N-methylmorpholine (1358 g, 13.4 mol) was added dropwise over about 3 hours to the reaction solution, followed by stirring for 1 hour at −7° C. The resulting slurry was filtered, and the residue on the filter was washed with 1600 g of isopropyl acetate. The obtained two filtrates were combined and sufficiently stirred to give a solution of 3-bromo-3-buten-2-one in isopropyl acetate (6993 g, content: 27.5%, yield: 96.1%).

(Step 2)

To 2-hydroxy-1,4-naphthoquinone (800 g, 4.59 mol), acetonitrile (880 g) and DBU (720 g, 4.73 mol) were added, and then the solution of 3-bromo-3-buten-2-one in isopropyl acetate (2490 g, fineness: 684 g, 4.59 mol) cooled to −15° C. to −10° C. was added dropwise over about 2 hours at 40±10° C. Ethanol (720 g) was added, and then DBU (216 g, 1.42 mol) was added dropwise at 20° C. to the reaction solution. Oxygen diluted to 6% with nitrogen was blown into the reaction solution at about 1 L per minute for 19 hours, and then a slurry was filtered to give a wet crystal. The wet crystal was washed with ethanol (680 g), 50% ethanol-water (800 g), and ethanol (680 g), sequentially, and then dried under reduced pressure to give a crude crystal of 2-acetyl-4H,9H-naphtho[2,3-b]furan-4,9-dione (524 g, 2.18 mol, HPLC purity: 98.9 area %) (yield: 47.4%). Overall yield based on methyl vinyl ketone: 45.6%.

$^1$H-NMR (400 MHz, DMSO-$d_6$) δ: 2.60 (3H, s), 7.90-7.94 (2H, m), 8.04 (1H, s), 8.12-8.17 (2H, m).

Example 2: Purification Methods of a Crude Crystal of 2-acetyl-4H,9H-naphtho[2,3-b]furan-4,9-dione Example 2-1

To a crude crystal of 2-acetyl-4H,9H-naphtho[2,3-b]furan-4,9-dione (5.00 g, 20.82 mmol, HPLC purity: 99.58 area %), anisole (150 g) and silica gel (0.50 g) were added, and the suspension was stirred for 2 hours at 100° C. By hot filtration of the suspension, the silica gel was removed to give a filtrate. The obtained filtrate was concentrated under vacuum at 70° C. to 80° C. to evaporate anisole (100 g). Subsequently, n-heptane (68.5 g) was added dropwise over 1 hour at 45° C. to 50° C. to the concentrated filtrate. The solution was cooled to 0° C., and then a slurry was filtered to give a wet crystal. The wet crystal was washed twice with ethyl acetate (20 g) cooled to 4° C., and then dried under reduced pressure to give a crystal of 2-acetyl-4H,9H-naphtho[2,3-b]furan-4,9-dione (4.77 g, 19.86 mmol, HPLC purity: 99.90 area %) (yield: 95.4%). Ethyl acetate (90.2 g) was added to the obtained crystal (4.00 g, 16.65 mmol), followed by reflux for 6 hours. The solution was cooled to room temperature and then filtered to give a wet crystal. The wet crystal was washed with ethyl acetate (12 g), and then dried under reduced pressure to give a crystal of 2-acetyl-4H,9H-naphtho[2,3-b]furan-4,9-dione (3.84 g, 15.99 mmol, HPLC purity: 99.96 area %) (yield: 96.0%). Overall yield based on methyl vinyl ketone: 37.7%.

Example 2-2

To a crude crystal of 2-acetyl-4H,9H-naphtho[2,3-b]furan-4,9-dione (5.00 g, 20.82 mmol, HPLC purity: 98.95 area %), anisole (150 g) and silica gel (0.50 g) were added. The mixture was warmed up to 100° C., and then by hot filtration, the silica gel was removed to give a filtrate. The obtained filtrate was concentrated under vacuum at 70° C. to 80° C. to evaporate anisole (100 g). A mixed solvent of o-xylene (25 g) and n-butanol (57.6 g) was added to the concentrated filtrate. The mixture was warmed up to 95° C., and then cooled to 0° C. to form a slurry. The resulting slurry was filtered to give a wet crystal. The wet crystal was washed twice with ethyl acetate (20 g) cooled to 0 to 5° C., and then dried under reduced pressure to give a crystal of 2-acetyl-4H,9H-naphtho[2,3-b]furan-4,9-dione (4.63 g, 19.27 mmol, HPLC purity: 99.97 area %) (yield: 92.6%).

Example 2-3

To a crude crystal of 2-acetyl-4H,9H-naphtho[2,3-b]furan-4,9-dione (5.00 g, 20.82 mmol, HPLC purity: 98.95 area %), anisole (150 g) and silica gel (0.50 g) were added. The mixture was warmed up to 100° C., and then by hot filtration, the silica gel was removed to give a filtrate. The obtained filtrate was concentrated under vacuum at 70° C. to 80° C. to evaporate anisole (100 g). n-Butanol (81 g) was added to the concentrated filtrate. The mixture was warmed up to 112° C., and then cooled to 0° C. to form a slurry. The slurry was filtered to give a wet crystal. The wet crystal was washed twice with ethyl acetate (20 g) cooled to 0 to 5° C., and then dried under reduced pressure to give a crystal of 2-acetyl-4H,9H-naphtho[2,3-b]furan-4,9-dione (4.70 g, 19.57 mmol, HPLC purity: 99.85 area %) (yield: 94.0%).

Example 2-4

To a crude crystal of 2-acetyl-4H,9H-naphtho[2,3-b]furan-4,9-dione (1.00 g, 4.16 mmol, HPLC purity: 98.95 area %), anisole (30 g) and silica gel (0.10 g) were added. Hot filtration was performed at 100° C. to remove the silica gel and give a filtrate. The obtained filtrate was concentrated under vacuum at 70° C. to 80° C. to evaporate anisole (20 g). Isobutyl acetate (17.5 g) was added to the concentrated filtrate. The mixture was warmed up to 110° C., and then cooled to 0° C. to form a slurry. The slurry was filtered to give a wet crystal. The wet crystal was washed twice with ethyl acetate (4 g) cooled to 0 to 5° C., and then dried under reduced pressure to give a crystal of 2-acetyl-4H,9H-naphtho[2,3-b]furan-4,9-dione (0.91 g, 3.79 mmol, HPLC purity: 99.88 area %) (yield: 91.0%).

Example 2-5

To a crude crystal of 2-acetyl-4H,9H-naphtho[2,3-b]furan-4,9-dione (5.00 g, 20.82 mmol, HPLC purity: 99.59 area %), anisole (150 g) and silica gel (0.50 g) were added. The mixture was warmed up to 100° C., and then hot filtration was performed to remove the silica gel and give a filtrate. The obtained filtrate was concentrated under vacuum at 70° C. to 80° C. to evaporate anisole (100 g). o-Xylene (88 g) was added to the concentrated filtrate. The mixture was warmed up to 91° C., and then cooled to 0° C. to form a slurry. The slurry was filtered to give a wet crystal. The wet crystal was washed twice with ethyl acetate (20 g) cooled to 0 to 5° C., and then dried under reduced pressure to give a crystal of 2-acetyl-4H,9H-naphtho[2,3-b]furan-4,9-dione (4.55 g, 18.94 mmol, HPLC purity: 99.95 area %) (yield: 91.0%).

Example 3: Crystallization of 2-acetyl-4H,9H-naphtho[2,3-b]furan-4,9-dione with ethyl acetate To 2-acetyl-4H,9H-naphtho[2,3-b]furan-4,9-dione (10.00 g, 41.6 mmol) obtained in Example 2, ethyl acetate (225.5 g) was added, followed by heating at reflux for 6 hours. After cooling to 25° C., a slurry was filtered to give a wet crystal, and the wet crystal was washed with ethyl acetate (30 g). The obtained wet crystal was dried under reduced pressure to give a crystal of 2-acetyl-4H,9H-naphtho[2,3-b]furan-4,9-dione (9.66 g, 39.97 mmol, HPLC purity: 99.95 area %) (yield: 96.0%).

Comparative Example 1: Production Method of 2-acetyl-4H,9H-naphtho[2,3-b]furan-4,9-dione As a comparative example, 2-acetyl-4H,9H-naphtho[2,3-b]furan-4,9-dione was produced in accordance with the method described in Patent Literature 3. Specifically, it is as follows.

To a 300 mL flask containing dichloromethane (40 mL) cooled to −2° C., methyl vinyl ketone (16.1 g, 0.23 mol) was added, and then bromine (36.7 g, 0.23 mol) was added dropwise over 25 minutes at 2 to 3° C. The reaction solution was washed with water (50 mL), and then the organic layer was dried over anhydrous sodium sulfate (5 g). After removing the anhydrous sodium sulfate, the organic layer was concentrated. The resulting residue (48.8 g) was transferred to a 1 L flask using DMF (40 mL), and cooled to −2° C. DBU (27.3 g, 0.18 mol) was added dropwise over 15 minutes to the DMF solution, and then DMF (50 mL) and 2-hydroxy-1,4-naphthoquinone (31.4 g, 0.18 mol) were added. The reaction mixture was warmed up to room temperature under an air atmosphere. To the reaction solution, DBU (25.8 g, 0.17 mol) was added dropwise over 45 minutes at room temperature, and then DMF (50 mL) was added. After the reaction solution was stirred for about 3 hours at room temperature, it was cooled to 0° C., and water (500 mL) was added thereto. The precipitated compound was collected by filtration and then was washed with water (80 mL), 5% sodium carbonate aqueous solution (80 mL), water (80 mL), 2% acetic acid aqueous solution (80 mL), and ethanol (80 mL), sequentially, to give 2-acetyl-4H,9H-naphtho[2,3-b]dihydrofuran-4,9-dione (21.1 g, 0.087 mol) (yield: 37.8%).

To a 500 mL flask, 2-acetyl-4H,9H-naphtho[2,3-b]dihydrofuran-4,9-dione (10.0 g, 41.3 mmol), ethanol (250 mL), and DBU (5.1 g, 34 mmol) were added, followed by heating at reflux for 30 minutes under an air atmosphere. After cooling the reaction solution to 0° C., water (250 mL) was added, and the precipitated crystal was obtained by filtration. The crystal was washed with water (10 mL), 2% acetic acid aqueous solution (10 mL), and ethanol (10 mL), sequentially, and then dried under reduced pressure to give a crystal of 2-acetyl-4H,9H-naphtho[2,3-b]furan-4,9-dione (3.17 g, 13.2 mmol, HPLC purity: 99.70 area %) (yield: 32.0%). Overall yield based on methyl vinyl ketone: 12.1%.

As described above, the present invention is illustrated by preferable embodiments of the present invention. However, it will be understood that the scope of the present invention should be interpreted only by the claims. It will be understood that the contents of patents, patent applications, and other literatures cited herein should be incorporated herein by reference as if their contents per se are specifically described herein.

INDUSTRIAL APPLICABILITY

The use of the production method of the present invention enables safe and inexpensive production of 2-acetyl-4H,9H-naphtho[2,3-b]furan-4,9-dione in a high yield and with high purity that is useful as a medicament.

The invention claimed is:

1. A compound of 2-acetyl-4H,9H-naphtho[2,3-b]furan-4,9-dione which is obtained by a process comprising the following steps (c) and (d):
   (c) reacting 3-bromo-3-buten-2-one, 2-hydroxy-1,4-naphthoquinone, and a base in the presence of a non-alcohol, non-ketone-based solvent A, and adding an alcohol-based solvent B and/or water to obtain a crystal of 2-acetyl-4H,9H-naphtho[2,3-b]furan-4,9-dione; and
   (d) dissolving 2-acetyl-4H,9H-naphtho[2,3-b]furan-4,9-dione obtained in the step (c) in a non-alcohol-based solvent C, followed by adding an adsorbent to purify the 2-acetyl-4H,9H-naphtho[2,3-b]furan-4,9-dione;
   wherein the purity of the compound is not less than 99.85 area % by HPLC.

2. The compound according to claim 1, wherein in the step (c), an oxidant is added to a reaction solution after the addition of the alcohol-based solvent B and/or water.

3. The compound according to claim 2, wherein the oxidant is at least one selected from the group consisting of oxygen, hydrogen peroxide, sodium hypochlorite, sodium chlorite, chlorine, iodine, nitric acid, and potassium nitrate.

4. The compound according to claim 3, wherein the oxidant is oxygen.

5. The compound according to claim 1, wherein in the step (c), a gas having an oxygen concentration of 1-25% is added to the reaction solution after the addition of the alcohol-based solvent B and/or water.

6. The compound according to claim 1, wherein the process further comprises the following step (e) after the step (d):
   (e) removing the adsorbent used in the step (d) and evaporating the non-alcohol-based solvent C.

7. The compound according to claim 6, wherein the process further comprises the following step (f) after the step (e):
   (f) crystallizing 2-acetyl-4H,9H-naphtho[2,3-b]furan-4,9-dione obtained in the step (e) by adding at least one crystallization solvent D selected from the group consisting of a hydrocarbon-based solvent, an alcohol-based solvent, an acid-based solvent, an ester-based solvent, an ether-based solvent, and water, to obtain 2-acetyl-4H,9H-naphtho[2,3-b]furan-4,9-dione.

8. The compound according to claim 7, wherein the process further comprises the following step (g) after the step (f):
   (g) slurrying 2-acetyl-4H,9H-naphtho[2,3-b]furan-4,9-dione obtained in the step (f) with ethyl acetate to form a crystal of 2-acetyl-4H,9H-naphtho[2,3-b]furan-4,9-dione.

9. The compound according to claim 1, wherein the non-alcohol, non-ketone-based solvent A used in the step (c) is at least one selected from the group consisting of a halogen-based solvent, an amide-based solvent, a nitrile-based solvent, a sulfoxide-based solvent, an ether-based solvent, an ester-based solvent, and a hydrocarbon-based solvent.

10. The compound according to claim 9, wherein the non-alcohol, non-ketone-based solvent A used in the step (c) is at least one selected from the group consisting of chloroform, dichloromethane, carbon tetrachloride, monochlorobenzene, N,N-dimethylacetamide, N,N-dimethylformamide, N-methyl-2-pyrrolidone, acetonitrile, propionitrile, dimethyl sulfoxide, diethyl sulfoxide, diisopropyl ether, tert-butyl methyl ether, cyclopentyl ethyl ether, cyclopentyl methyl ether, tetrahydrofuran, 2-methyltetrahydrofuran, 1,4-dioxane, anisole, methyl acetate, ethyl acetate, propyl acetate, butyl acetate, toluene, and xylene.

11. The compound according to claim 10, wherein the non-alcohol, non-ketone-based solvent A used in the step (c) is at least one selected from the group consisting of chloroform, monochlorobenzene, N,N-dimethylacetamide, N-methyl-2-pyrrolidone, acetonitrile, tert-butyl methyl ether, tetrahydrofuran, 2-methyltetrahydrofuran, anisole, ethyl acetate, toluene, and xylene.

12. The compound according to claim 11, wherein the non-alcohol, non-ketone-based solvent A used in the step (c) is at least one selected from the group consisting of monochlorobenzene and acetonitrile.

13. The compound according to claim 1, wherein in the step (c), 0.8 equivalent to 1.2 equivalents of 2-hydroxy-1,4-naphthoquinone is reacted in a molar ratio to 3-bromo-3-buten-2-one.

14. The compound according to claim 13, wherein in the step (c), 0.9 equivalent to 1.1 equivalents of 2-hydroxy-1,4-naphthoquinone is reacted in a molar ratio to 3-bromo-3-buten-2-one.

15. The compound according to claim 1, wherein the base used in the step (c) is diazabicycloundecene.

16. The compound according to claim 15, wherein diazabicycloundecene used in the step (c) has a molar ratio of 0.9 equivalent to 5.0 equivalents to 3-bromo-3-buten-2-one.

17. The compound according to claim 16, wherein in the step (c), 0.9 equivalent to 1.5 equivalents of diazabicycloundecene in a molar ratio to 3-bromo-3-buten-2-one is added to the reaction solution of 3-bromo-3-buten-2-one and 2-hydroxy-1,4-naphthoquinone, and after stirring for one minute to three hours, 0.01 equivalent to 1.0 equivalent of diazabicycloundecene is further added in a molar ratio to 3-bromo-3-buten-2-one.

18. The compound according to claim 1, wherein the alcohol-based solvent B used in the step (c) is methanol, ethanol, 1-propanol, 2-propanol, n-butyl alcohol, or isobutyl alcohol, or mixtures thereof.

19. The compound according to claim 18, wherein the alcohol-based solvent B used in the step (c) is methanol or ethanol, or mixtures thereof.

20. The compound according to claim 1, wherein the non-alcohol-based solvent C used in the step (d) is at least one selected from the group consisting of an ether-based solvent, an amide-based solvent, a ketone-based solvent, a halogen-based solvent, a sulfoxide-based solvent, an ester-based solvent, a hydrocarbon-based solvent, and a nitrile-based solvent.

21. The compound according to claim 18, wherein the non-alcohol-based solvent C used in the step (d) is at least one selected from the group consisting of chloroform, dichloromethane, carbon tetrachloride, monochlorobenzene, N,N-dimethylacetamide, N,N-dimethylformamide, N-methyl-2-pyrrolidone, acetonitrile, propionitrile, dimethyl sulfoxide, diethyl sulfoxide, diisopropyl ether, tert-butyl methyl ether, cyclopentyl ethyl ether, cyclopentyl methyl ether, tetrahydrofuran, 2-methyltetrahydrofuran, 1,4-dioxane, anisole, methyl acetate, ethyl acetate, propyl acetate, butyl acetate, toluene, xylene, acetone, methyl ethyl ketone, and methyl isobutyl ketone.

22. The compound according to claim 20, wherein the non-alcohol-based solvent C used in the step (d) is at least one selected from the group consisting of N,N-dimethylacetamide, N,N-dimethylformamide, anisole, ethyl acetate, propyl acetate, and butyl acetate.

23. The compound according to claim 20, wherein the non-alcohol-based solvent C used in the step (d) is anisole.

24. The compound according to claim 1, wherein the adsorbent used in the step (d) is at least one selected from the group consisting of activated alumina, zeolite, activated carbon, and silica gel.

25. The compound according to claim 24, wherein the adsorbent used in the step (d) is silica gel.

26. The compound according to claim 1, wherein the adsorbent used in the step (d) is a 0.01 to 0.3-fold amount in a weight ratio to 2-acetyl-4H,9H-naphtho[2,3-b]furan-4,9-dione.

27. The compound according to claim 26, wherein the adsorbent used in the step (d) is a 0.02 to 0.2-fold amount in a weight ratio to 2-acetyl-4H,9H-naphtho[2,3-b]furan-4,9-dione.

28. The compound according to claim 7, wherein the crystallization solvent D used in the step (f) is at least one selected from the group consisting of n-heptane, xylene, n-butanol, isobutyl acetate, toluene, cyclohexane, acetic acid, methanol, ethanol, 1-propanol, 2-propanol, n-butyl alcohol, isobutyl alcohol, and water.

29. The compound according to claim 28, wherein the crystallization solvent D used in the step (f) comprises n-heptane.

30. The compound according to claim 28, wherein the crystallization solvent D used in the step (f) comprises xylene.

31. The compound according to claim 28, wherein the crystallization solvent D used in the step (f) comprises n-butanol.

32. The compound according to claim 28, wherein the crystallization solvent D used in the step (f) comprises isobutyl acetate.

33. The compound according to claim 1, wherein the process further comprises the following steps (a) and (b) before the step (c):
(a) reacting 3-buten-2-one and bromine to form 3,4-dibromobutan-2-one; and
(b) reacting 3,4-dibromobutan-2-one obtained in the step (a) with a base to undergo dehydrobromination thereby forming 3-bromo-3-buten-2-one.

34. The compound according to claim 33, wherein the base used in the step (b) is at least one selected from the group consisting of triethylamine, diisopropylethylamine, N-methylpyrrolidine, 1,4-diazabicyclo[2.2.2]octane, N-methylmorpholine, and inorganic bases.

35. The compound according to claim 34, wherein the base used in the step (b) is N-methylmorpholine.

36. The compound according to claim 1, wherein the purification temperature is 30° C. to 100° C.

37. The compound according to claim 1, wherein the purity of the compound is not less than 99.95 area % by HPLC.

38. A medicament comprising the compound of claim 1.

39. 2-acetyl-4H,9H-naphtho[2,3-b]furan-4,9-dione, the purity of which is not less than 99.85 area % by HPLC.

40. 2-acetyl-4H,9H-naphtho[2,3-b]furan-4,9-dione, the purity of which is not less than 99.95 area % by HPLC.

41. A medicament comprising 2-acetyl-4H,9H-naphtho[2,3-b]furan-4,9-dione of claim 39.

* * * * *